(12) United States Patent
Munn

(10) Patent No.: US 7,975,695 B2
(45) Date of Patent: Jul. 12, 2011

(54) ORAL AIRWAY

(76) Inventor: Myron Munn, Beatrice, NE (US)

( * ) Notice: Subject to any disclaimer, the term of this patent is extended or adjusted under 35 U.S.C. 154(b) by 778 days.

(21) Appl. No.: 12/012,098

(22) Filed: Jan. 31, 2008

(65) Prior Publication Data

US 2008/0121229 A1    May 29, 2008

Related U.S. Application Data

(63) Continuation of application No. 11/584,978, filed on Oct. 23, 2006.

(51) Int. Cl.
*A61M 11/00* (2006.01)
(52) U.S. Cl. .............. 128/207.14; 128/207.15
(58) Field of Classification Search ............ 128/200.26, 128/207.14, 207.15
See application file for complete search history.

(56) References Cited

U.S. PATENT DOCUMENTS

| | | | |
|---|---|---|---|
| 2,127,215 A | 8/1938 | Gwathmey | |
| 2,599,521 A | 6/1952 | Berman | |
| 2,705,959 A * | 4/1955 | Elmore | 128/207.14 |
| 2,765,959 A | 4/1955 | Elmore | |
| 3,306,298 A | 2/1967 | Raimo | |
| 3,398,747 A | 8/1968 | Raimo | |
| 3,419,004 A * | 12/1968 | Berman | 128/207.14 |
| 3,568,680 A | 3/1971 | Raimo | |
| 3,576,187 A | 4/1971 | Oddera | |
| 3,756,244 A | 9/1973 | Kinnear et al. | |
| 3,908,665 A | 9/1975 | Moses | |
| 3,926,196 A | 12/1975 | Bornhorst et al. | |
| 3,930,507 A | 1/1976 | Berman | |
| D261,442 S | 10/1981 | Anderson | |
| 4,363,320 A | 12/1982 | Kossove | |
| 4,919,126 A * | 4/1990 | Baildon | 128/207.14 |
| 6,196,224 B1 | 3/2001 | Alfery | |

* cited by examiner

*Primary Examiner* — Steven O Douglas
(74) *Attorney, Agent, or Firm* — Dennis L. Thomte; Thomte Patent Law Office LLC

(57) ABSTRACT

An improved Guedel Oral Airway for providing an air passage to a patients trachea. The oral airway includes a tubular member which is generally elliptical in cross section and having a straight section and a curved section with the tubular member having a curved lower wall member extending from the center of the bottom wall portion of the tubular member outwardly and away from the tubular member. The cross-section of the lower wall member is generally an inverted V-shape in cross-section with the side edges thereof being positioned outwardly of the end wall portions of the tubular member.

3 Claims, 2 Drawing Sheets

ORAL AIRWAY

CROSS-REFERENCE TO RELATED APPLICATION

This is a continuation-in-part application of Petitioner's earlier application Ser. No. 11/584,978 filed Oct. 23, 2006, entitled "ORAL AIRWAY", the disclosure of which is hereby incorporated herein by reference.

BACKGROUND OF THE INVENTION

1. Field of the Invention

This invention relates to an oral airway and more particularly to an improved Guedel Oral Airway which truly represents an improvement in the oral airway art.

2. Description of the Related Art

In modern anesthesia practice, oral airways are used primarily for two reasons. The first reason is that after intubation of the trachea, an oral airway is placed to prevent a patient from biting down on the endotracheal tube and thus occluding the endotracheal tube. The second and primary reason for the use of an oral airway in the practice of anesthesia is to elevate the tongue against the floor of the mouth to create a larger opening in the mouth to facilitate the utilization of positive pressure ventilation using an anesthesia mask after a patient has been given medications to induce general anesthesia. The drugs normally used to induce general anesthesia may greatly decrease or altogether stop the patient's own spontaneous respiratory effort. Therefore, the Anesthesia Practitioner must immediately begin assisting or controlling the patient's ventilation.

It is the patients undergoing general anesthesia that the inventor, an Anesthesia Practitioner, has noted, and personally experienced, occasional difficulties in maintaining a patient's airway and the ability to ventilate the patient. The inventor has over 27 years of experience with over 10,000 general anesthetics administered and during this time has encountered many patients of all ages which were difficult to ventilate with an anesthesia mask after induction of general anesthesia. This has happened even after proper placement of the recommended size of oral airway. Anyone who has practiced anesthesia for some time has experienced the same difficulties. Anesthesia Practitioners are all taught the 'tricks of the trade' in how to ventilate patients after induction of general anesthesia including a variety of physical adjustments to the anesthetized patient such as elevation of the jaw and extension of the patient's neck. If the patient cannot be adequately ventilated after induction of general anesthesia, life-threatening problems may develop such as hypoxia, hypercarbia, cardiac arrhythmias and even death.

Once general anesthesia has been induced, one of the main impediments to adequately ventilating a patient with positive pressure ventilation, after placement of an oral airway, is the relaxation of the soft tissue structures in the hypo-pharynx. These structures tend to collapse, thus obstructing airflow. This inward collapsing occurs both front to back and side to side, thus greatly decreasing the size of the oral opening through which the Anesthesia Practitioner may ventilate the patient. This anatomical relaxation is fairly consistent with every patient who undergoes a general anesthetic. However, there is a physical characteristic of some patients which greatly increases the difficulty of mask ventilation—that characteristic is obesity. As mentioned before, the inventor has administered over 10,000 general anesthetics during 27 years of practicing anesthesia and has noted the increasing incidence of obesity in both the pediatric and adult population. These obese patients present an increased level of difficulty to the Anesthesia Practitioner in the area of airway management. Obese patients tend to have larger, thicker tongues along with more redundant soft tissue in the oropharyngeal area. Obese patients also tend to have thicker necks, so it is more difficult to hyperextend the neck and lift the jaw to facilitate adequate ventilation after general anesthesia is induced. In discussions with other Anesthesia Practitioners, the inventor has perceived a common concern that the oral airways currently available do not adequately address the growing problem of obesity in the population.

As stated, it is well known to utilize an oral airway for the purpose of aiding the breathing of unconscious patients. The Guedel Oral Airway, and other similar devices, is employed in the practice of anesthesia and other areas of respiratory medicine by insertion of the oral airway into the mouth and pharynx of a patient to provide a channel for respiratory purposes, particularly in unconscious patients such as those who have been administered a general anesthetic. It is the purpose of the oral airway to prevent respiratory obstruction by preventing collapse of the pharyngeal tissues and/or obstruction of the pharynx by the tongue.

The Guedel Oral Airway and later devices are available to the medical professional in a number of different sizes for use in all sizes of patients from premature infants to large adults. However, each size constitutes a unitary member which may not itself be adjusted in size, shape, or contour. Thus, conventional airways are substantially rigid structures which may not be altered in use to fit particular patients, particular problems, or unusual anatomic anomalies or structures. The Guedel Oral Airway has served Anesthesia Practitioners well for many years, but the physical characteristics of patients have changed over the last several years while the Guedel Oral Airway remains the same.

The Guedel Oral Airway comes in various sizes from 40 mm to 120 mm in incremental steps of 10 mm (i.e., 40 mm, 50 mm, 60 mm, 70 mm, 80 mm, 90 mm, 100 mm, 110 mm, and 120 mm). These sizes are roughly correlated to general anatomic dimension described as the distance from the exterior of the front teeth to the back of the oropharynx. So, correspondingly, a 40 mm Guedel Oral Airway is probably an appropriate size for a premature infant whereas a 120 mm Guedel Oral Airway is probably appropriate for a very large adult, and a 90 mm Guedel Oral Airway is generally used on a medium adult patient. If the patient is very obese and has a thick tongue and has a large amount of soft tissue in the oropharynx, the 90 mm oral airway may not adequately elevate the tongue because it is not wide enough side to side to provide enough support for the tongue. In this case, a 100 mm Guedel Oral Airway (which is wider side to side) may provide the additional support for the tongue that is needed to open the airway, but it cannot be used because the longer structure of the airway (100 mm) may not fit in the patients mouth. The 100 mm oral airway would extend too far outside of the patients mouth, thus placing an anesthesia mask over the patients face to obtain a good mask seal in order to ventilate the patient with positive pressure would be very difficult, if not impossible. This has happened to the inventor many times in his career. The usual scenario is someone who is of very short stature and very obese. These people many times need the width and depth of a 100 mm Guedel Oral Airway, but the length of an 80 mm Guedel Oral Airway. This would greatly facilitate the ability to ventilate this patient after induction of general anesthesia. The inventor has overcome this problem in the past by actually inserting two 80 mm Guedel Oral Airways on these types of patients or sometimes one 90 mm Guedel Oral Airway and one 80 mm Guedel Oral Airway. In this way you are able to achieve enough side to side tongue support to adequately ventilate the patient until you are ready to place an endotracheal tube. Inserting two oral airways into the patient is sometimes adequate but can be awkward. Therefore, a new type of oral airway is needed for these patients.

SUMMARY OF THE INVENTION

Accordingly, the present invention provides improvements to the Guedel Oral Airway which will provide better elevation of the tongue against the floor of the mouth by way of: 1) the addition of an inverted "V" shaped member to the lower curved member of the curved section of the Guedel Oral Airway; and 2) the inverted "V" shaped member would have greater side-to-side width than the corresponding Guedel Oral Airway. The greater width of the inverted "V" shaped member on the curved lower member of the curved section of the Improved Guedel Oral Airway will give better lift and support to the tongue, thus increasing both the anterior-posterior dimension, and the lateral dimension, of the patients airway opening. This will greatly facilitate the positive pressure ventilation of the patient under general anesthesia.

By altering these characteristics of the Guedel Oral Airway, but not altering the length or the radius of the curve of the airway, the Improved Guedel Oral Airway sizes of this invention would be interchangeable with the Guedel Oral Airway sizes. For instance, in a situation where you would normally use a 90 mm Guedel Oral Airway, the 90 mm Improved Guedel Oral Airway of this invention would be appropriate, but would give better tongue support and consequently a larger opening of the patient's airway to facilitate easier ventilation of the patient. This would be especially helpful in obese patients with large tongues, but would also be useful for all patients being administered general anesthesia.

It is therefore a principal object of the invention to provide an improved oral airway.

A further object of the invention is to provide a modification of the Guedel Oral Airway which provides increased side-to-side support of the tongue.

Still another object of the invention is to provide an improved oral airway which provides better elevation of the tongue against the floor of the mouth.

Still another object of the invention is to provide an improved oral airway which greatly increases the lateral support of the tongue as compared to the conventional Guedel Oral Airway.

These and other objects will be apparent to those skilled in the art.

DETAILED DESCRIPTION OF THE PREFERRED EMBODIMENT

Figure 1:
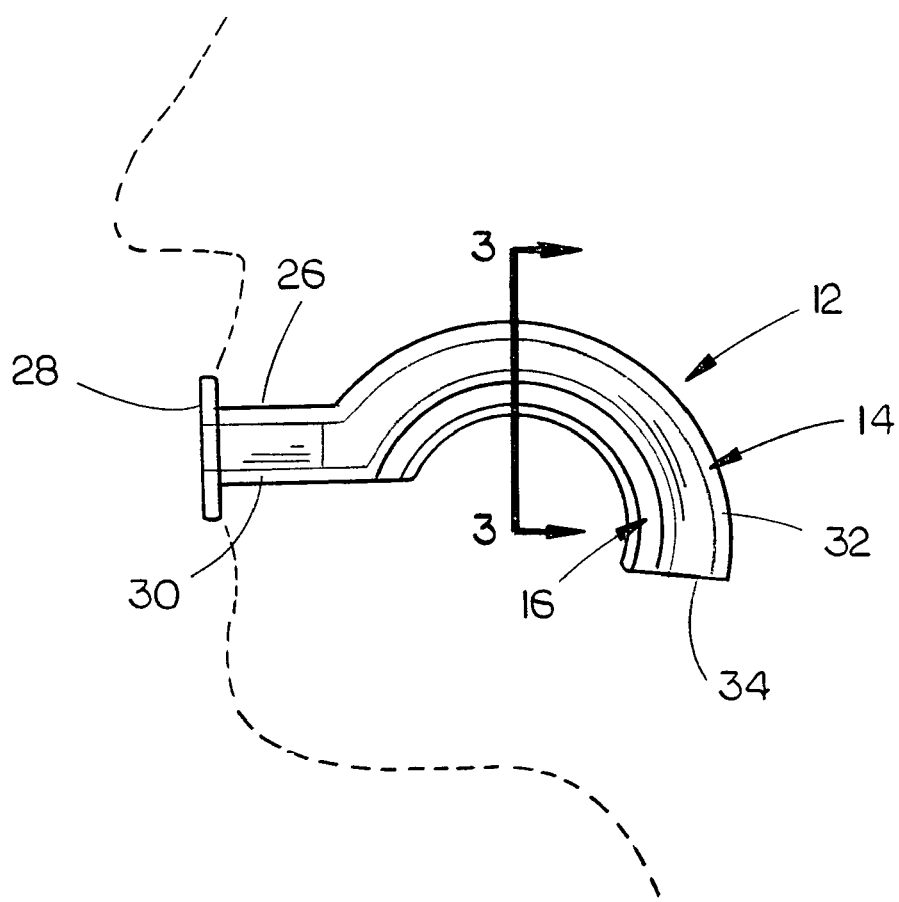
FIG. 1 is a side view of the oral airway of this invention positioned within a patients mouth.
Figure 2:
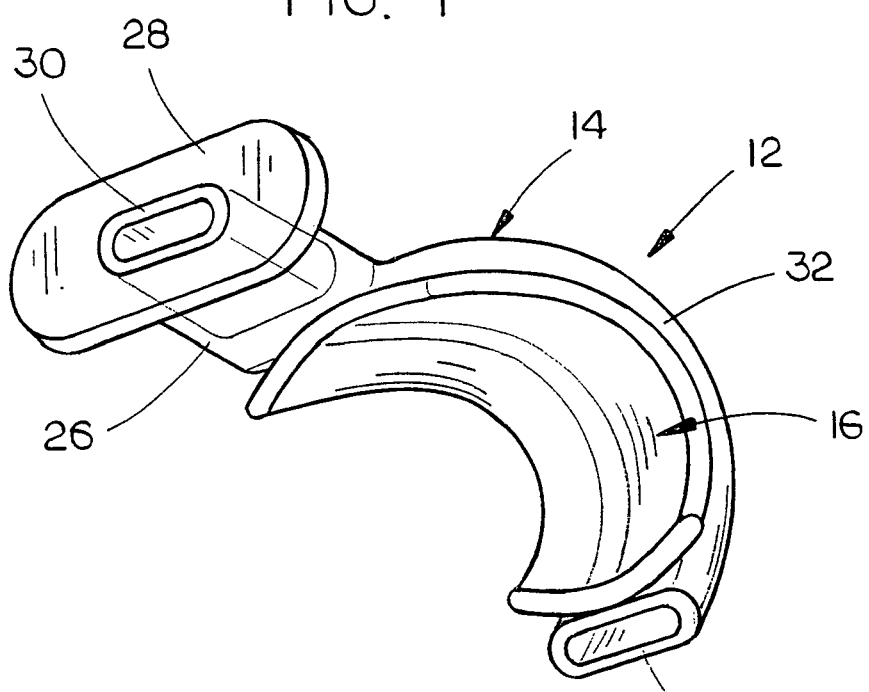
FIG. 2 is a perspective view of the oral airway of this invention.
Figure 3:
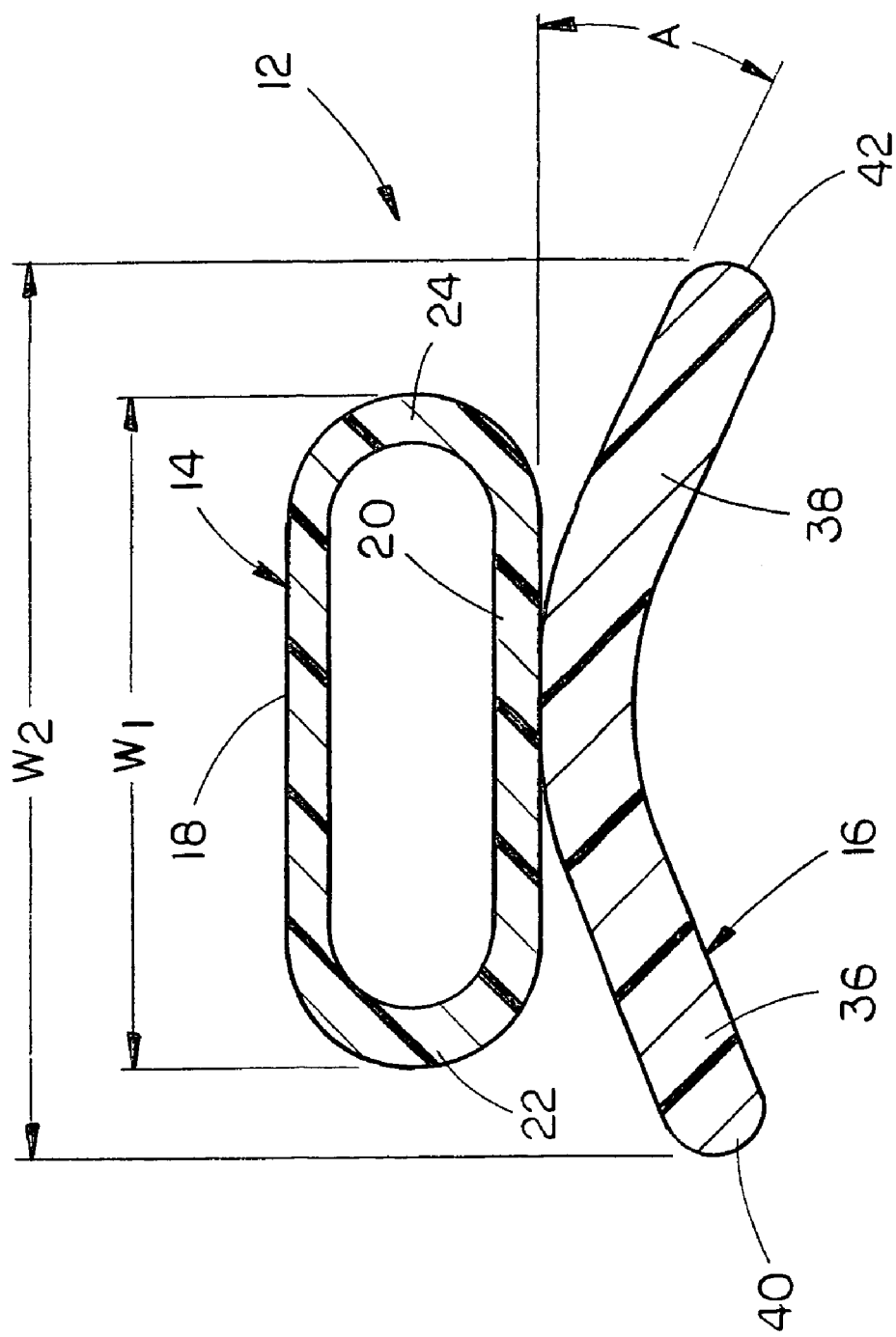
FIG. 3 is a sectional view of the oral airway of this invention as seen on line 3-3 of FIG. 1.

In the drawings the numeral 12 refers generally to the preferred embodiment of this invention. Airway 12 includes a tubular member 14 and a lower wall member 16. Tubular member 14 has a generally elliptical cross-section and includes an upper wall portion, 18, lower wall portion, 20, and sidewall portions 22 and 24 (FIG. 3). Tubular member 14 includes a straight section 26 having an outwardly extending flange 28 at the outer end thereof. Preferably, the outer end of the straight section 26 is reinforced with a bite-block member 30. Tubular member 14 also includes a curved section 32 which extends from the inner end of the straight portion 26 to its terminal end 34. The structure described so far is normally referred to as a Guedel Oral Airway.

The lower wall member 16 is joined to the lower wall portion 20 at the center width thereof and has a pair of wing members 36 and 38 which extend therefrom in a diverging manner to generally define a "V" cross-section as seen in FIG. 3. Preferably, the wing members 36 and 38 extend at an angle with respect to the lower wall portion 20 which is approximately 25 degrees and referred to as "A" in FIG. 3. The side edges 40 and 42 of wing members 36 and 38 are preferably positioned outwardly of the end wall portions 22 and 24 having a distance therebetween generally designated as W2. The distance between the outer sides of tubular member 14 is referred to generally in FIG. 3 as W1. Preferably, the width of W2 is approximately 40% greater than the width of W1.

Therefore, the present invention provides modifications to the Guedel Oral Airway which provides better elevation to the tongue against the floor of the mouth by way of:
  (1) Increasing the distance the tongue is elevated against the floor of the mouth thus increasing the anterior-posterior dimension of the airway opening;
  (2) The greater width of the lower wall member 35 will give better support to the tongue laterally, thus increasing the side to side dimension of the airway opening;
  (3) The elevation of the lower curved member 35 into a generally inverted "V" shape increases the lateral support of the tongue. By altering the Guedel Oral Airway, but not altering the length of the radius of the curve of the airway, better tongue support is provided and consequently a larger opening of the patients airway to facilitate easier ventilation of the patient. This would be especially helpful in obese patients with large tongues but would also be helpful for all patients being administered general anesthesia.

Thus it can be seen that the invention accomplishes at least all of its stated objectives.

I claim:

1. An oral airway to provide an air passage to a patient's trachea, comprising:
    an elongated tubular member having inner and outer ends and including a straight section at its outer end adapted to fit between the patient's teeth and a curved section adapted to fit over the patient's tongue and extending to the oropharyngeal area;
    said tubular member being generally elliptical in cross-section and having an upper wall portion, a lower wall portion, and opposite side wall portions;
    said outer end of said tubular member having an outwardly extending flange;
    said flange adapted to externally overlie the lips of the patient;
    and an elongated, curved lower member joined to said lower wall portion of said curved section of said tubular member;
    said lower member having a generally inverted V-shape in cross-section;
    said curved lower member having substantially the same width for its entire length;
    said curved lower member defining diverging wing members, having side edges which extend outwardly from said lower wall portion of said curved section of said tubular member;
    the distance between the side edges of said wing members being constant for substantially the entire length of said curved lower member.

2. The oral airway of claim 1 wherein said side edges of said wing members are spaced outwardly of said side wall portions of said tubular member.

3. The oral airway of claim 2 wherein the width of said curved lower member is approximately 40% greater than the width of said tubular member.

* * * * *